United States Patent
Egan et al.

(10) Patent No.: US 11,642,003 B2
(45) Date of Patent: May 9, 2023

(54) DISINFECTING FLOOR MAT FOR CLEANING THE BOTTOMS OF SHOES

(71) Applicants: Jennifer Egan, Centennial, CO (US); Dawson Swan, Loveland, CO (US)

(72) Inventors: Jennifer Egan, Centennial, CO (US); Dawson Swan, Loveland, CO (US)

(*) Notice: Subject to any disclaimer, the term of this patent is extended or adjusted under 35 U.S.C. 154(b) by 378 days.

(21) Appl. No.: 17/006,516

(22) Filed: Aug. 28, 2020

(65) Prior Publication Data
US 2021/0076901 A1 Mar. 18, 2021

Related U.S. Application Data

(60) Provisional application No. 63/017,045, filed on Apr. 29, 2020, provisional application No. 62/900,783, filed on Sep. 16, 2019.

(51) Int. Cl.
| | |
|---|---|
| *A47L 23/26* | (2006.01) |
| *A47L 23/20* | (2006.01) |
| *A61L 2/26* | (2006.01) |
| *A61L 2/18* | (2006.01) |
| *A61L 101/34* | (2006.01) |

(52) U.S. Cl.
CPC .............. *A47L 23/266* (2013.01); *A47L 23/20* (2013.01); *A61L 2/18* (2013.01); *A61L 2/26* (2013.01); *A61L 2101/34* (2020.08); *A61L 2202/15* (2013.01); *A61L 2202/17* (2013.01)

(58) Field of Classification Search
CPC ........ A47L 23/266; A47L 23/26; A47L 23/20; A61L 2202/17
See application file for complete search history.

(56) References Cited

U.S. PATENT DOCUMENTS 3,067,913 A * 12/1962 Matthew ................. A47L 23/24
422/291
5,071,628 A 12/1991 Alazet
5,556,685 A 9/1996 Swicegood, Jr.
(Continued)

FOREIGN PATENT DOCUMENTS

BR 202016003258 U2 * 8/2017
WO WO8702564 A1 * 5/1987

OTHER PUBLICATIONS

Machine translation: BR202016002358U2; Marconato et al. (Year: 2017).*

*Primary Examiner* — Natasha N Campbell
(74) *Attorney, Agent, or Firm* — Leyendecker & Lemire, LLC

(57) ABSTRACT

A disinfecting floor mat having a disinfecting wet station (or wet side) onto which a user may step and wet the bottoms of his/her shoes with a disinfecting and/or cleaning solution are described. The wet section can comprise a shallow pool over which an elastomeric cover is provided that has small holes. slits or other openings distributed thereon permitting the solution to flow therethrough when the cover is stepped upon to make contact with the shallow pool bottom. A reservoir of cleaning solution can be provided that is in fluid communication with the shallow pool to help ensure it remains full. Optionally, the floor mat can further include a drying section (or dry side) located next to the wet section to permit a user to substantially dry the bottoms of his/her shoes after disinfecting the shoe bottoms in the wet section.

20 Claims, 9 Drawing Sheets

(56) References Cited

U.S. PATENT DOCUMENTS

| | | |
|---|---|---|
| 6,146,588 A | 11/2000 | Deighton |
| 8,973,197 B2 | 3/2015 | Omidi |
| 9,622,642 B2 | 4/2017 | Braaten |
| 9,968,238 B2 | 5/2018 | Patel |
| 2004/0078909 A1 | 4/2004 | Coppa |
| 2009/0098031 A1* | 4/2009 | Crist ................. A47L 23/02 422/292 |
| 2014/0223684 A1 | 8/2014 | Hawkins |
| 2014/0295537 A1 | 10/2014 | Omidi |
| 2016/0015844 A1 | 1/2016 | Collins |
| 2017/0128606 A1 | 5/2017 | Jackson |
| 2017/0143186 A1 | 5/2017 | Vasquez |
| 2018/0042449 A1 | 2/2018 | Ori |
| 2019/0133414 A1* | 5/2019 | Barnhill ............. A47L 23/02 |

* cited by examiner

DISINFECTING FLOOR MAT FOR CLEANING THE BOTTOMS OF SHOES

RELATED APPLICATIONS

The present application claims priority to and incorporates fully by reference the following two provisional applications both having the same inventor and both being entitled "Disinfecting Floor Mat for Cleaning the Bottoms of Shoes": U.S. Provisional Patent application No. 62/900,783 filed on 16 Sep. 2019; and U.S. Provisional Patent application No. 63/017,045 filed on 29 Apr. 2020.

BACKGROUND

When a person wearing shoes enters a building from outside, the bottoms of his/her shoes may be covered with bacteria, virus spores and other pathogens carried in dirt or other particulate. If the shoes are not removed, the contaminates can be tracked into the building. People may be requested to remove their shoes, but many people are uncomfortable removing them. In other instances, removing shoes might not be a viable option as they would have to go barefoot and expose their feet to pathogens on the floor's surface.

Shoe mats do a reasonable job of removing larger particulate, but they do not disinfect or sanitize the bottoms of shoes. Mats have been proposed that include liquid reservoirs whether as shallow pools or saturating an open celled foam; however, these often exhibit drawbacks. For instance, the sanitizing liquid can evaporate quickly requiring frequent replacement, or the liquid can splash from its receptacle on to adjoining flooring surfaces.

DETAILED DESCRIPTION

Figure 1:
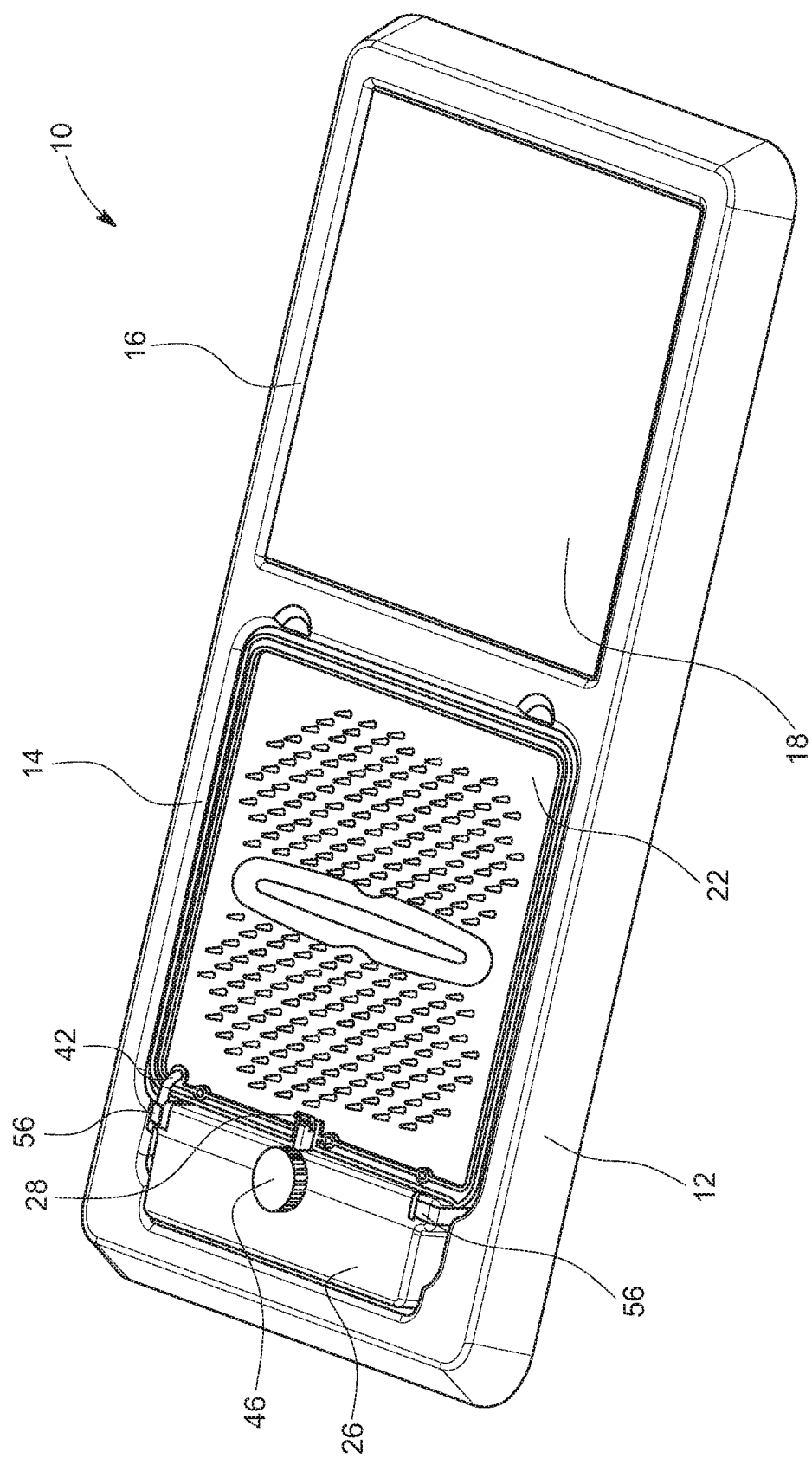
FIG. 1 is a perspective front side top view of a disinfecting mat assembly according to an embodiment of the present invention.

Embodiments of a disinfecting floor mats having a disinfecting wet section (wet station) onto which a user may step and wet the bottoms of his/her shoes with a disinfecting and/or cleaning solution are described. The wet section can comprise a shallow pool over which an elastomeric cover is provided that has small holes. slits or other openings distributed thereon permitting the solution to flow therethrough when the cover is stepped upon to make contact with the shallow pool bottom. A reservoir of cleaning solution can be provided that is in fluid communication with the shallow pool to help ensure it remains full. Some embodiments can further include a drying section (or dry side) located next to the wet section to permit a user to substantially dry the bottoms of his/her shoes after disinfecting the shoe bottoms in the wet section.

At least one embodiment comprises a mat base divided into wet and dry sections respectively. The wet section typically contains a pan which defines a shallow pool into which the disinfecting/cleaning liquid can be received. In some embodiments the solution comprises isopropyl alcohol. A flexible resilient and elastomeric cover is typically received over the pan and the shallow pool of liquid hindering the rapid evaporation of the liquid. As mentioned, the elastomeric cover typically has a plurality of holes distributed on the cover that extend through the cover. In some variations some of the holes can comprise wholly or partially self-sealing slits (or slots). In the variations having slits, the slits are sealed when in the cover is in its normal unflexed state preventing evaporation therethrough; however when flexed, such as when the cover is stepped upon, the slits at least partially open and allow liquid to pass upwardly therethrough. The cover can also include a suitable surface texture, such as nubbins, to help facilitate cleaning of shoe bottoms.

A drying pad is received in the dry section and secured therein by any suitable means, such as with hook and loop fasteners, or the surrounding walls of a recess formed in the mat base. The drying pad can include an absorbent section of carpet, a non-woven absorbent pad, a microfiber towel, a foam pad, or any other material or combination of materials configured to wick cleaning solution from the bottoms of shoes in contact therewith.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiments and are not necessarily intended to be construed as limiting.

The phrase "disinfecting solution" as used herein refers to any liquid solution that kills or destroys one or both of bacteria or viruses that come in contact with the solution. In at least one variation, the solution primarily comprises isopropyl alcohol, although solutions of other liquids can be utilized as well.

An Embodiment of a Disinfecting Floor Mat

A two section (or station) disinfecting floor mat assembly 10 is illustrated in FIG. 1. It comprises a mat base 12 with left and right recesses 14&16 (also referred to as wet side and dry side recesses respectively). The right recess typically receives a drying pad 18 used to dry off the bottoms of a user's shoes after he/she cleans his shoes in the wet side. A wet section subassembly is received in the left recess and typically comprises a shallow pan 20 (see FIG. 3) into which disinfecting solution is received, a elastomeric pan cover 22 for the pan that includes drain holes 24 (see FIG. 4A) or openings distributed thereon, an enclosed reservoir 26 for storing disinfecting solution, and a valve slide 28 to control the flow of solution from the reservoir to the pan to refill the pan. Clips 56 and threaded fasteners (not shown) are also provided to secure the primary components together.

Figure 2:
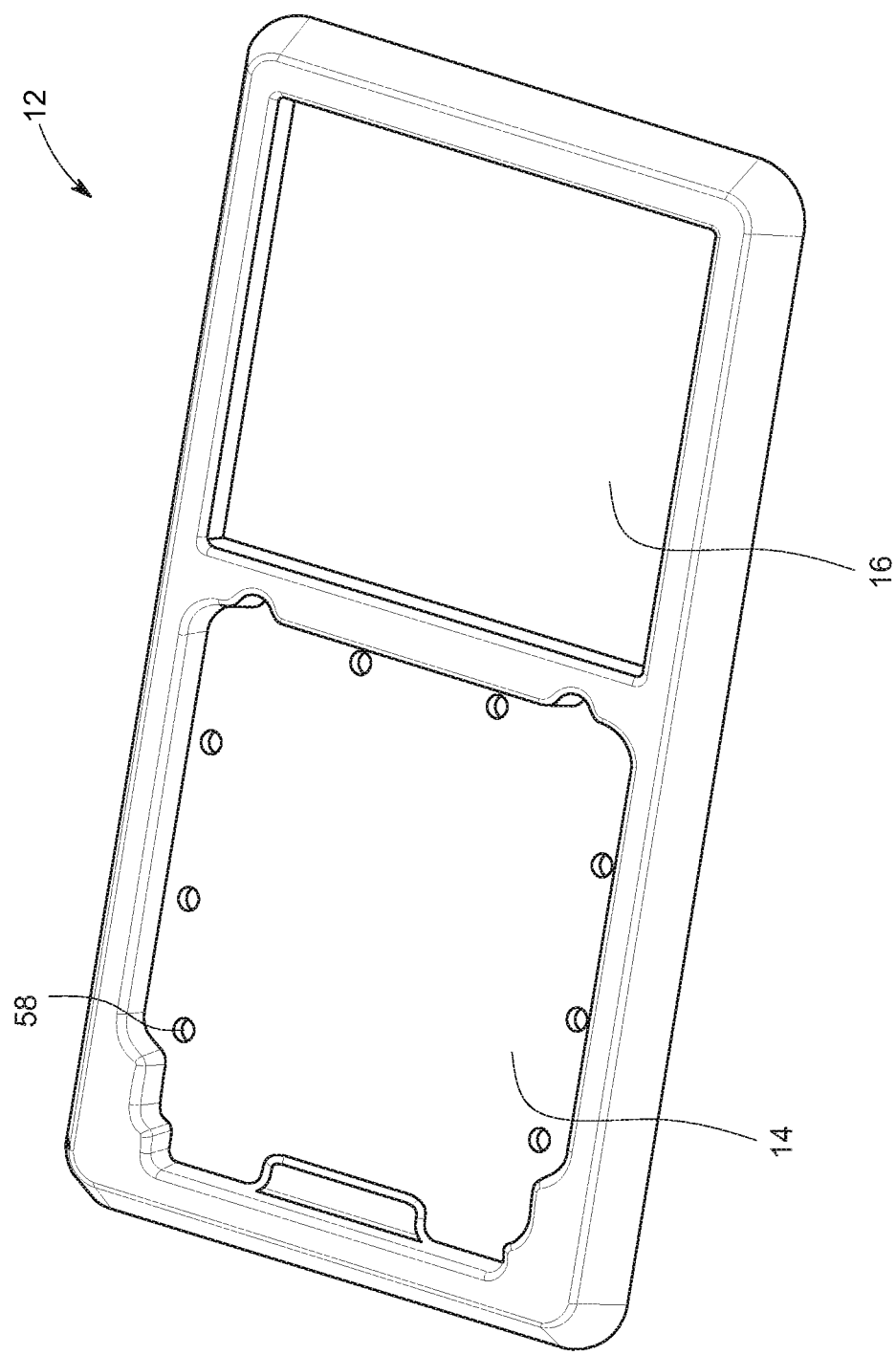
FIG. 2 is a perspective top view of a mat base of the disinfecting mat assembly according to one embodiment of the present invention.

The mat base 12 is best shown in FIG. 2. It can be made from any suitable material although typically it is comprised of a dense synthetic rubber or polyurethane foam. It is resilient when stepped upon but firm enough to retain its shape. Further, the rubber-like mat tends to have a high coefficient of frictions relative to harder plastics allowing it to stick to or grip the underlying surface of the floor and resist sliding around. The top surface of the mat base is defined by the adjacent left and right recesses 14 & 16. The right recess is typically configured to receive a drying pad and the left recess is typically configured to receive the wet section subassembly. Small round dimpled depressions 58 are provided in the bottom of the left recess that are provided to hold the heads of the threaded fasteners used to hold the elastomeric cover 22 to the shallow pan 20. As shown the edges of the base may be sloped. The dimensions of the mat base can vary significantly by are typically about 21" wide by 36" long and 1.5-3.5" tall.

The drying pad 18 as shown in FIG. 1 can be anyone of a variety of materials in a variety of forms and configurations. The drying pad is typically a foam or fibrous pad that is also absorbent. It may also include a rough or textured surface that acts to catch and help remove dirt and soil from the bottoms of shoes as they are wiped there upon. The pad can include, but is not limited to, a section of carpet or rug with upwardly extending bristles, a non-woven material, a woven sheet, such as sisal, and an open celled foam sheet. The pad can have several layers to help enhance its functionality, such as an absorbent underlayer topped with an abrasive scrubbing layer. In at least one embodiment the dry pad can comprise in whole or in part an antimicrobial/antibacterial microfiber material, such as a silver-infused product.

In at least one embodiment, the drying pad comprises an absorbent foam sheet of suitable thickness that is received in a fabric cover, such as one comprised of a microfiber material. The cover can be removable for replacement or to be washed. As can be appreciated the exposed surface of the microfiber fabric can be napped or tufted to increase absorbency and more effectively dry the bottoms of the shoes.

The raised sides of the right recess 16, which can vary in depth depending on the embodiment or variation, can secure and hold the pad in place. In some versions, hook material strips can be secured to the bottom surface of the recess to capture the fibers of the pad or loop material strips secured to the underside of the pad. In other versions, the base may have nubbins or spike-like protrusions that stick into the pad and help secure it in place. In yet other versions, the pad can be adhesively secured to base.

Figure 3A:
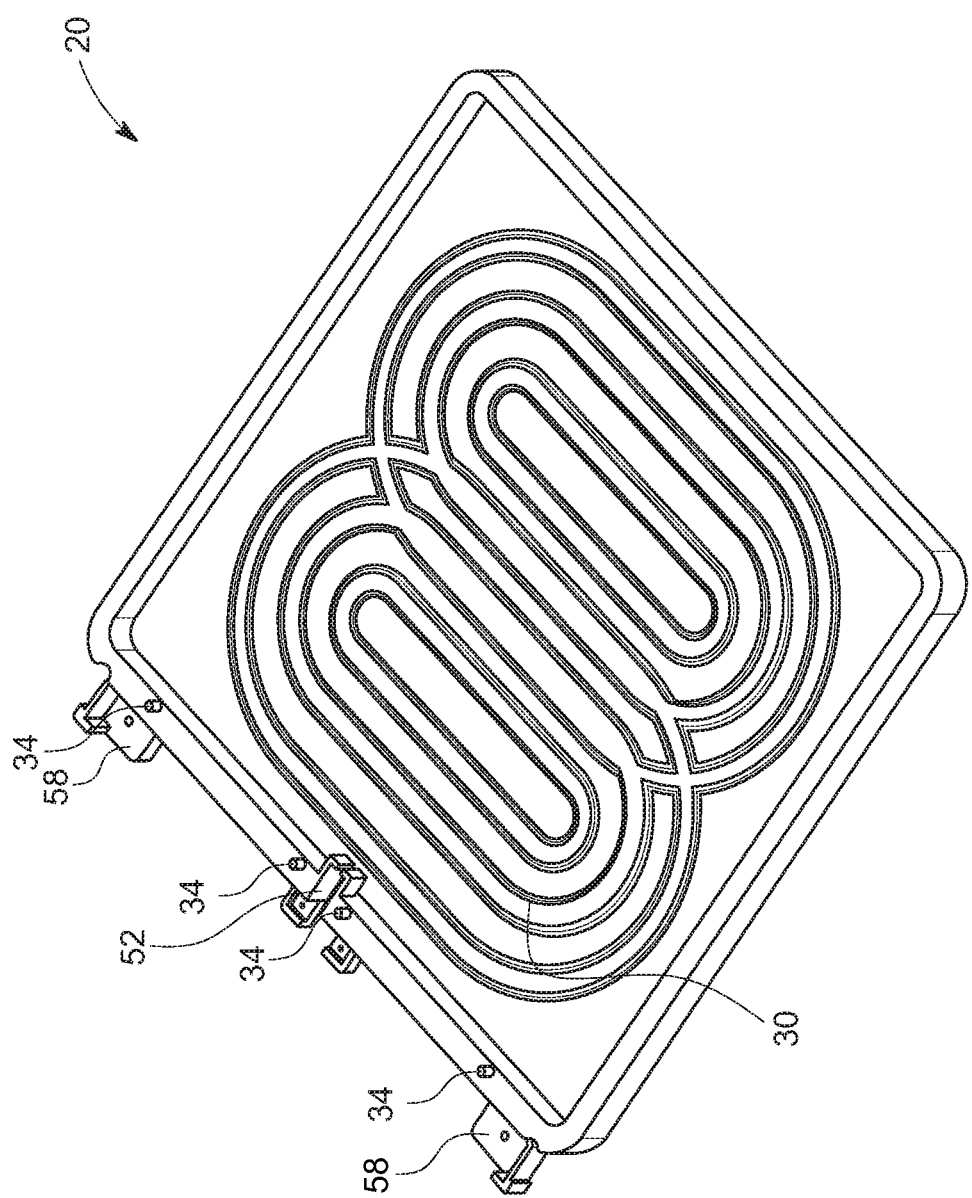
FIGS. 3A & B are perspective top and bottom views of a shallow pan of the disinfecting mat assembly according to one embodiment of the present invention.
Figure 3B:
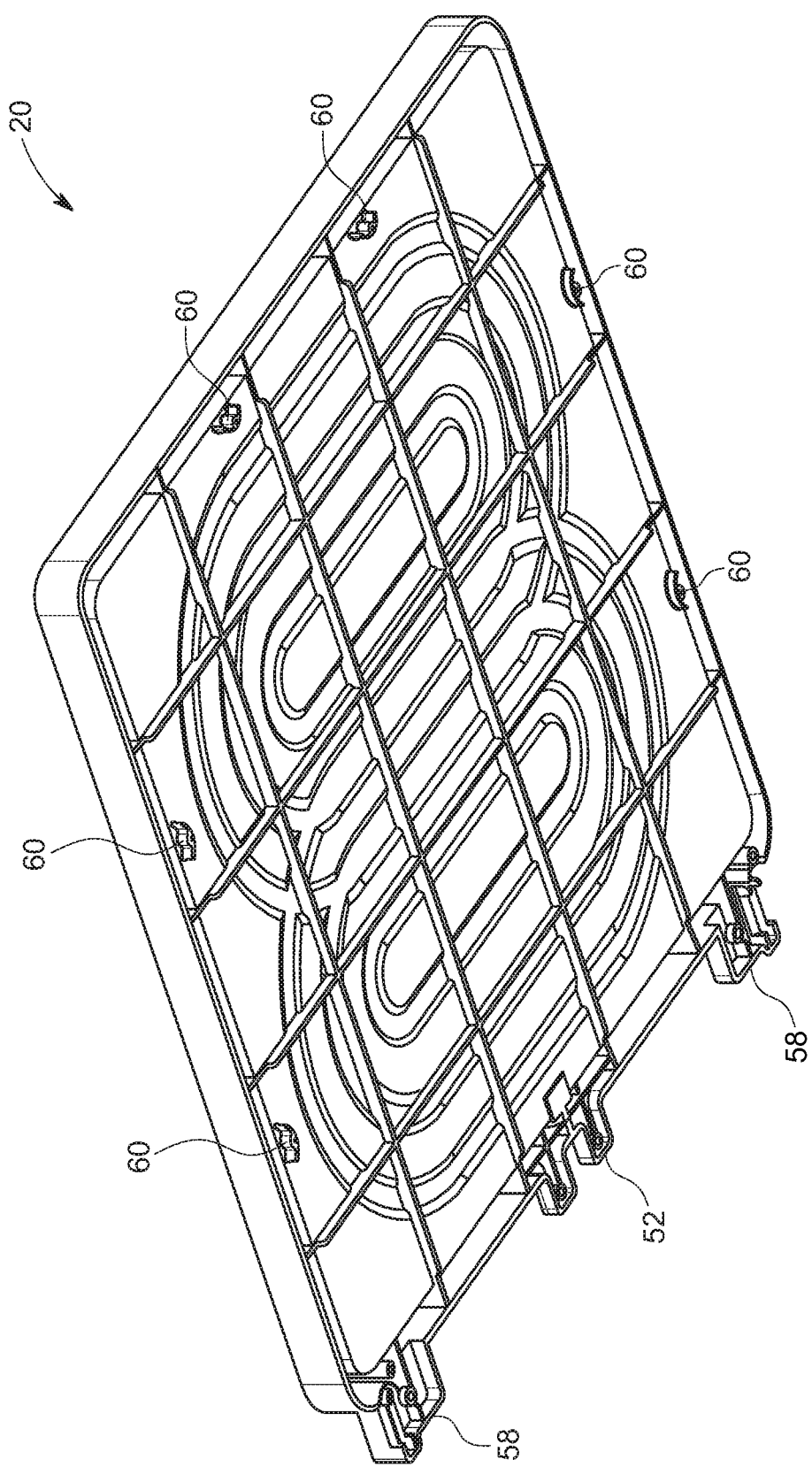

The wet section subassembly (or wet station) primarily comprises the pan 20, the pan cover 22, and the reservoir 26 and includes an on/off valve in the form of a valve slide 28 (or shut off gate) including associated conduit to permit fluid communication between the pan and reservoir. As mentioned threaded fasteners and two clips 56 can also be provided to secure the components together. The pan 20 as illustrated in FIG. 3A & B is typically comprised of a molded rigid plastic material and includes four sidewalls that encompass a pan bottom surface. Generally, a shallow pool of disinfecting solution resides in the pan. The bottom surface, as shown, can include raised ridges 30 that control the bottoming out of the elastomeric cover when the cover is stepped upon during use. Along the edge of the pan adjacent the reservoir, several molded pegs 34 can be provided that help secure the pan cover in place as is described further below.

Along one side of the pan, two outwardly-extending reservoir securing protrusions 58 are provided at the ends of the side to facilitate the attachment of the reservoir 26 to the pan through the use of the clips 56. Additionally, proximate the center of the pan, a slide receiver slot 52 is molded therein to receive an outlet protrusion 70 of the reservoir 26 as well as the valve slide 28. On the bottom side of the pan, a plurality of bosses 60 are provided that with the use of the threaded fasteners secure the elastomeric cover 22 to the pan as discussed further below.

Figure 4A:
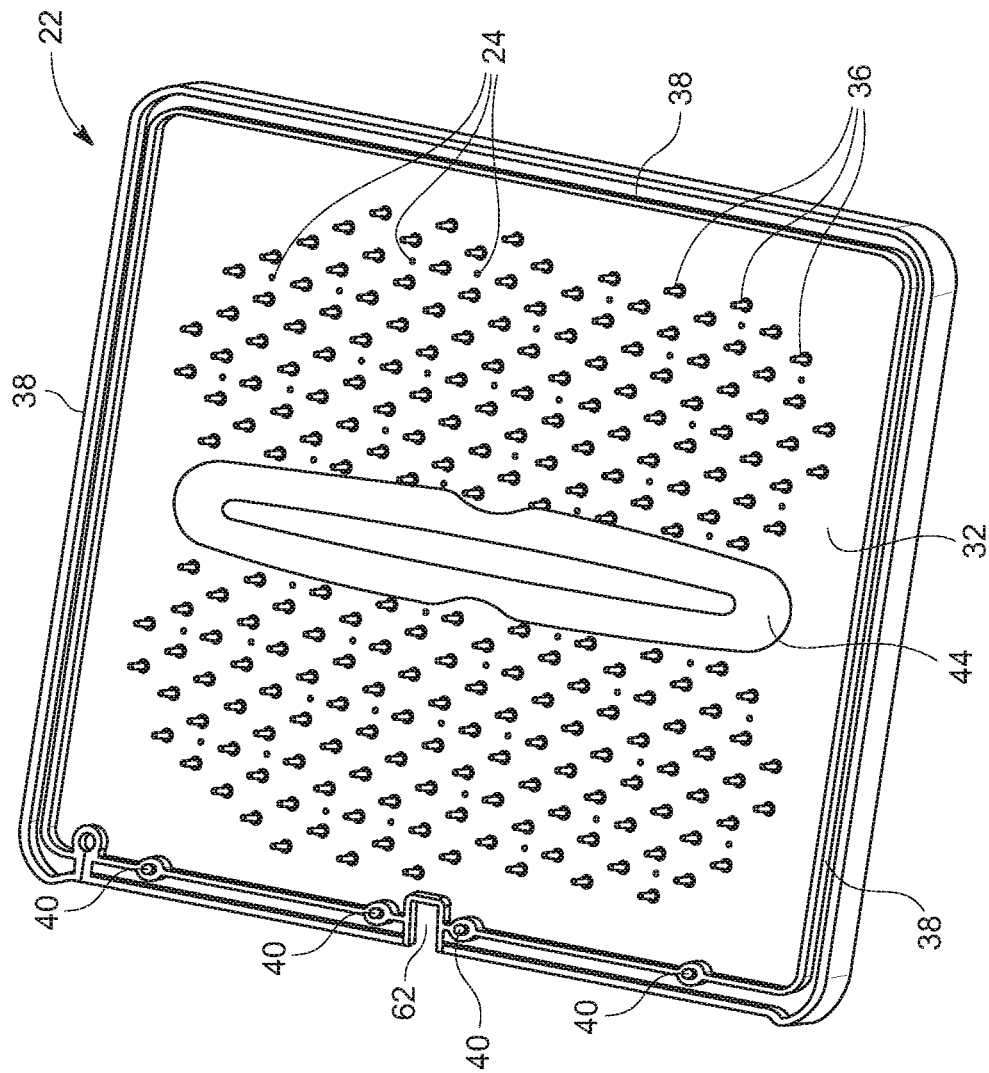
FIGS. 4A & B are perspective top and bottom views of an elastomeric pan cover of the disinfecting mat assembly according to one embodiment of the present invention.

The elastomeric pan cover 22 is best illustrated in FIGS. 4A & B. It can comprise an resilient elastomeric material including rubber and polyurethane, although in one embodiment the cover comprises a silicone material. The cover typically comprises a unitary piece comprising a top sheet 32 with drain holes 24 and nubbins 36 distributed over its surface and at least three sidewalls 38 configured to be received over the sidewalls of the pan 20 to help hold the top sheet tautly in place. As shown, the side of the cover adjacent the reservoir does not include a sidewall but includes a plurality of spaced holes 40 that are received over pegs 34 extending upwardly from the corresponding sidewall edge of the pan to further hold the top sheet tautly in place. A slot 62 is also provided along this side to provide a space for the reservoir outlet protrusion 70.

The upwardly-extending nubbins 36 are provided to help dislodge solid material from the bottoms of the shoes as the shoes are slid across them. The top sheet 32 is stretched when stepped upon, and the disinfecting solution permeates through the holes as the sheet is dunked in the shallow pool of disinfecting solution in the pan 20. As also shown, the top sheet also includes a slightly raised center section 44 that in use would generally be positioned between the left and right shoe of a user. The raised center inhibits solution from pooling near the center of the top sheet 32 after the user has stepped off of the sheet and presumably moved his feet and shoes over to the drying section of the mat assembly. The excess solution can drain back into the shallow pool in the pan 20 after the wet section has been used by way of the drain holes 24.

Figure 4B:
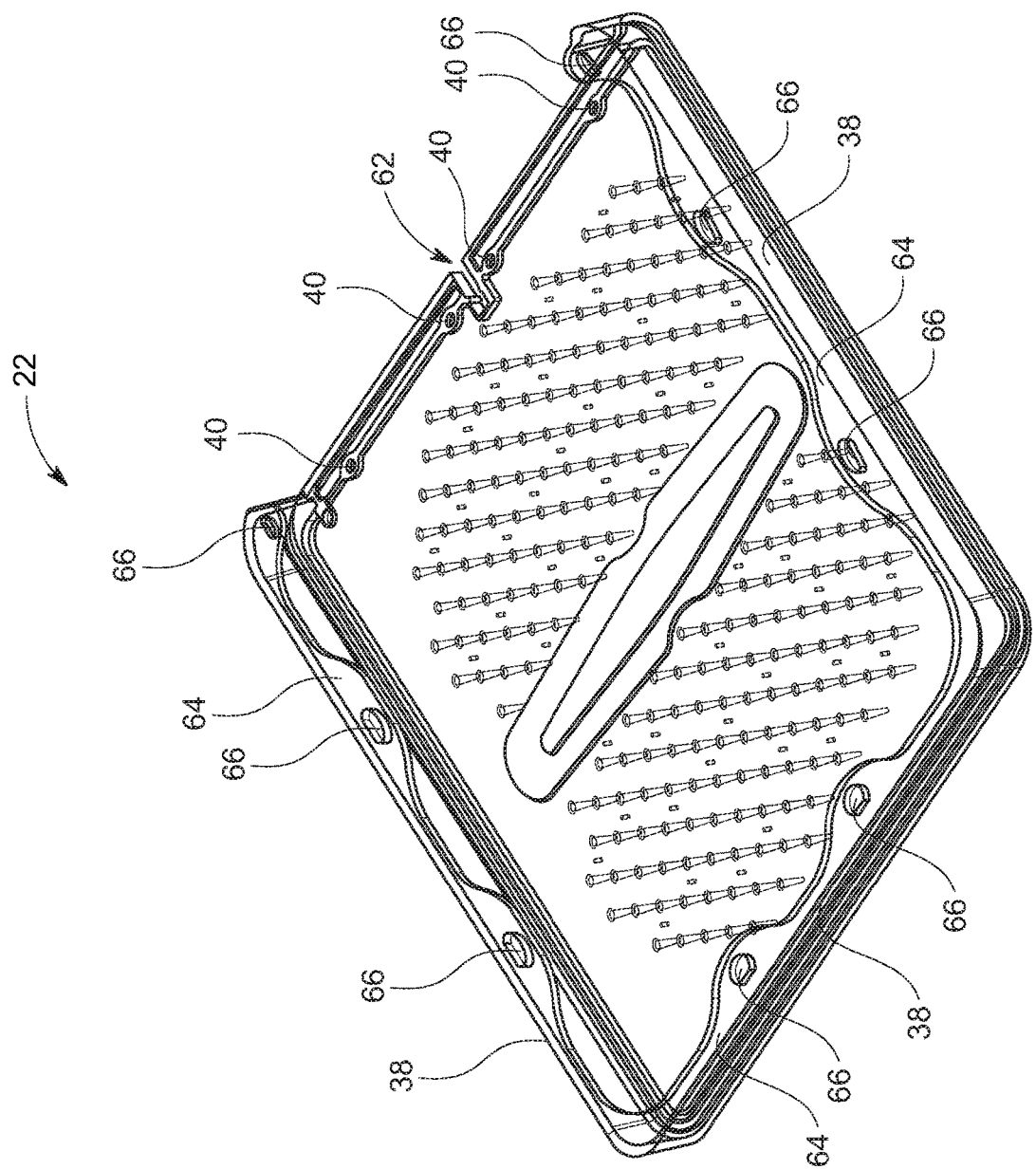

As can best be seen in FIG. 4B, a flange 64 extends orthogonally inwardly from the bottom edge of each sidewall 38 of the elastomeric cover 22. Distributed on these flanges are a plurality of boss openings 66 that correspond in placement with the plurality of bosses 60 on the bottom of the pan. To secure the cover to the pan, the cover boss openings are received over the pan boss openings and secured in place with the threaded fasteners with or without the use of a suitable washer.

Figure 5:
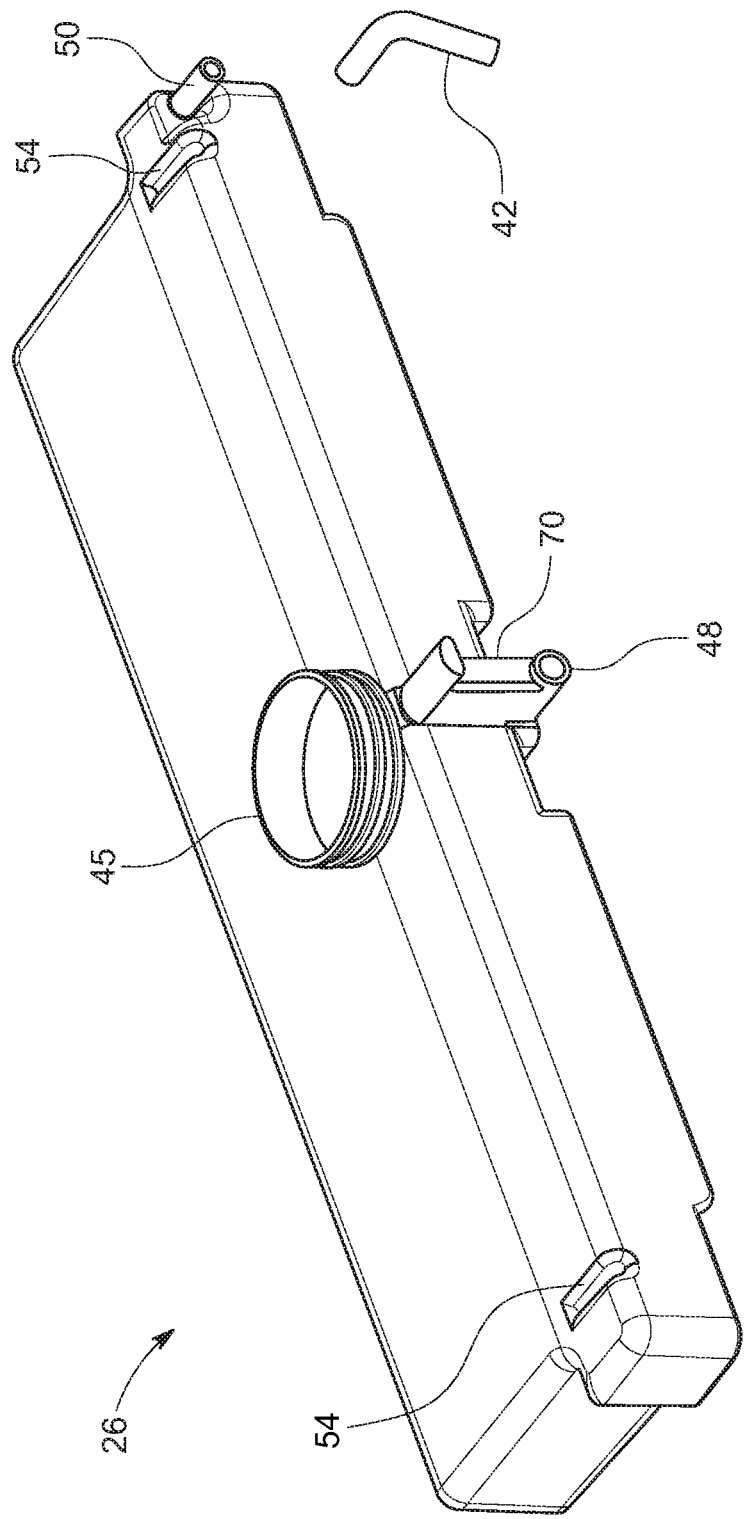
FIG. 5 is a right side top view of a fluid reservoir of the disinfecting mat assembly according to one embodiment of the present invention.

FIG. 5 is an illustration of the reservoir 26 in which disinfecting solution can be stored. An opening 45 is provided on the top that can be used to periodically fill the reservoir. A cap 46 can be provided to seal the reservoir as shown in FIG. 1. An outlet tube 48 is provided along one side of the container near its bottom through which the solution can flow into the pan 20 when the valve slide 28 is opened. An air inlet 50 is provided near the top of the reservoir. An L-shaped rigid tube 42 is provided that attaches to the air inlet and extends into the space between the pan 20 and the cover 22. This inhibits the creation of a vacuum or low pressure condition in the void that forms in the reservoir as fluid flows from the reservoir to the interior of the pan during a pan filling operation. Essentially, it ensures pressure in and out of the reservoir is equalized as solution flows from the reservoir into the pan.

Figure 7:
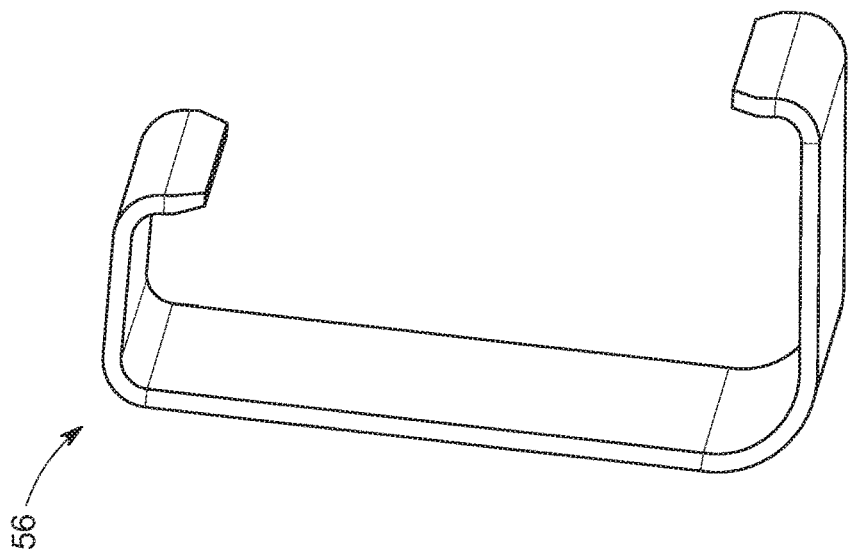
FIG. 7 is a perspective view of a securing clip of the disinfecting mat assembly according to one embodiment of the present invention.

The reservoir can be coupled to the pan subassembly by any suitable mechanism, but in the illustrated embodiment a pair of clips 56, such as illustrated in FIG. 7 are used. A bottom end of each clip is received into a slot provided on the bottom of the reservoir securing protrusions 58, and the top end of the clip is received in a slot 54 provided in the reservoir 26. Once connected, an outlet protrusion 70 of the reservoir is received into the slide receiver slot 52 of the pan 20. The placement of a clip holding the pan and reservoir together can be seen in FIG. 8.

Figure 6B:
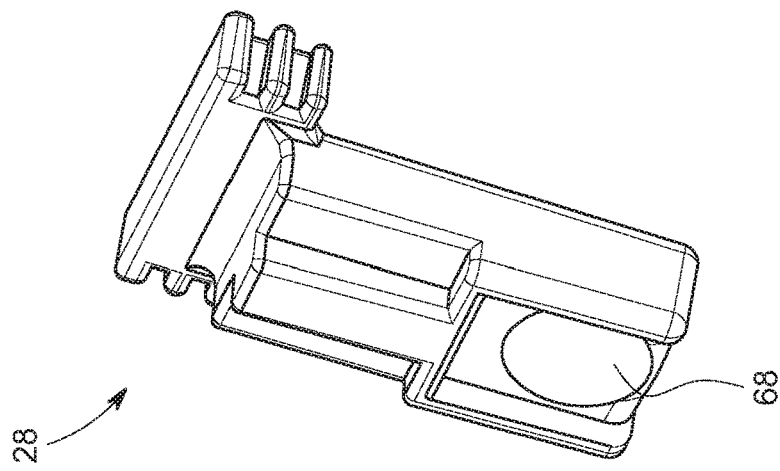
FIGS. 6A & B are front and back perspective views of the flow control valve slide according to one embodiment of the present invention.
Figure 6A:
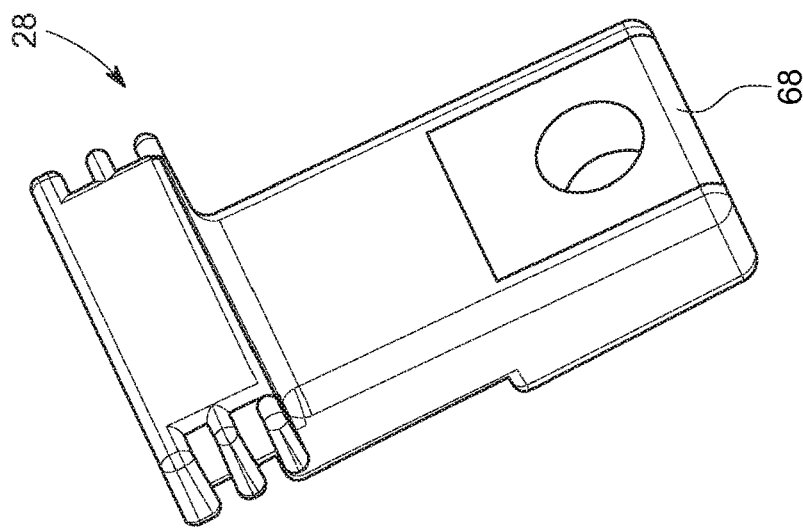
Figure 8:
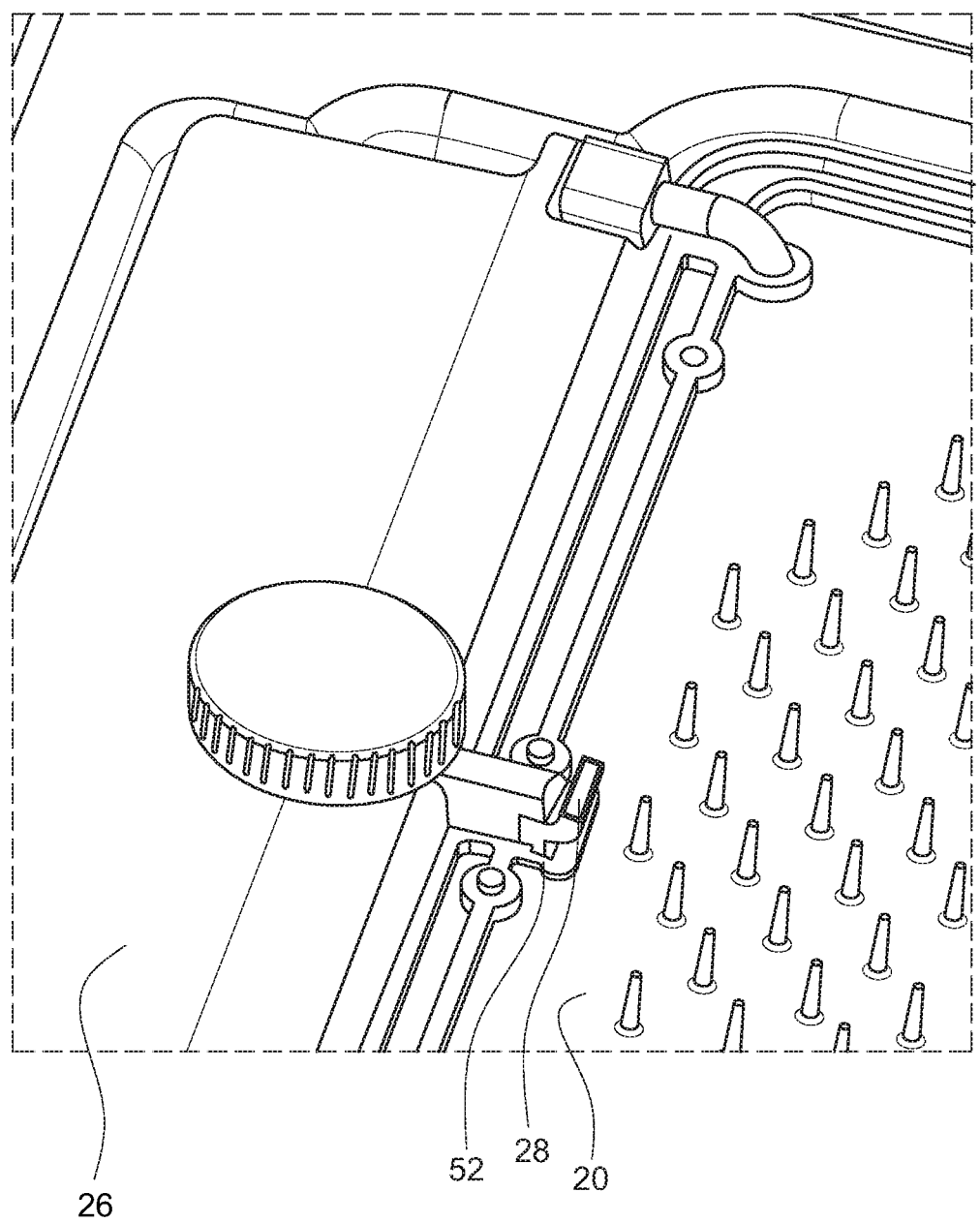
FIG. 8 is a close up perspective view of the disinfecting mat assembly illustrating the interconnection between the reservoir and the disinfecting pan according to one embodiment of the present invention.

FIGS. 6A & B are perspective front and back views of the valve slide 28. As can be seen, an elastomeric seal insert 68 can also be provided. The valve slide is slidably received in the slide receiver slot 52 molded into the shallow pan 20. When seated in the down position the seal insert substantially seals the outlet tube 48 preventing the flow of disinfecting solution into the pan from the reservoir 26. When removed or pulled upwardly into an unseated position, the insert seal is moved off of the outlet tube and disinfecting solution can flow from the reservoir into the pan. FIG. 8 illustrates the valve slide in the closed position in the slide receiver slot to seal the outlet tube.

A Method of Using Embodiments of the Disinfecting Mat Assembly

In use, a person entering a building steps on to the wet section of the mat assembly 10 and more specifically the elastomeric pan cover 22. The elastomeric pan cover flexes and stretches into the shallow pool contained in the pan 20 below. Disinfecting solution seeps through the holes 24 in the cover. The person can slide his/her feet back and forth across the nubbins 36 to work in the solution and scrub the bottom surface of the shoes. Next, the person can step on to the dry section wherein he/she can wipe the bottom of the shoes against the surface of the drying pad 18 to both dry the soles and further dislodge any particulate. Thereafter, the person can continue into the building with reduced concern of transferring pathogens, viruses, and bacteria to the floor therein.

Alternative Embodiments and Other Variations

The various embodiments and variations thereof described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

For instance variations are contemplated wherein the pan is integrated into mat base. Other variations may do away with a separate reservoir wherein the solution is contained in the pan alone and refilled occasionally. Other variations are contemplated wherein the flow of solution between the reservoir and the pan is automatically metered.

We claim:

1. A floor mat assembly for sanitizing the bottoms of shoes, the floor mat assembly comprising:
    a mat base with a dry side recess and a wet side recess next to the dry side recess;
    a drying pad received in the dry side recess; and
    a wet station received in the wet side recess, the wet station including (i) a pan for holding a pool of disinfecting solution, and (ii) an elastomeric cover covering the pan and the pool of disinfecting solution therein, the elastomeric cover having a plurality of openings being (a) integral to the elastomeric cover, (b) defined between a thickness of the elastomeric cover, and (c) distributed thereon;
    wherein the plurality of openings are normally closed and open to allow solution therethrough when the elastomeric cover is stepped upon and stretched.

2. The floor mat assembly of claim 1, wherein the plurality of openings comprise a plurality of holes.

3. The floor mat assembly of claim 1, wherein the elastomeric cover is tautly disposed over the pan.

4. The floor mat assembly of claim 1, wherein the elastomeric cover includes a plurality of raised nubbins distributed thereron.

5. The floor mat assembly of claim 1, wherein the elastomeric cover includes a raised center section substantially extending across a top surface of the elastomeric cover.

6. The floor mat assembly of claim 1, wherein the elastomeric cover is made of silicone.

7. The floor mat assembly of claim 1, wherein the mat base is comprised of an elastomeric foam.

8. The floor mat assembly of claim 1 further comprising a fluid reservoir configured to contain disinfecting solution, the fluid reservoir being in selective fluid communication with the pan.

9. The floor mat assembly of claim 8, wherein the fluid reservoir includes an outlet the outlet being selectively openable and closable by way of an on/off valve to control the flow of disinfecting solution from the reservoir into the pan.

10. The floor mat assembly of claim 9 wherein the on/off valve comprises a slide member.

11. The floor mat assembly of claim 8, wherein the pan is secured to the fluid reservoir with one or more clips.

12. The floor mat assembly of claim 8, wherein the elastomeric cover is defined by (i) three sidewalls adapted to be received over sidewalls of the pan, and (ii) a side adjacent the fluid reservoir not including a sidewall.

13. The floor mat assembly of claim 8, wherein the fluid reservoir includes an air inlet and an L-shaped rigid tube connected to the air inlet that extends into a space between the pan and the elastomeric cover.

14. The floor mat assembly of claim 1, wherein the pan has a bottom surface and includes one or more upwardly-extending raised ridges disposed thereon.

15. The floor mat assembly of claim 1, wherein the disinfecting solution comprises isopropyl alcohol.

16. The floor mat assembly of claim 1, wherein the drying pad comprises one of a section of carpet, a non-woven matting, and open cell foam.

17. A floor mat assembly for sanitizing the bottoms of shoes, the floor mat assembly comprising:
  a mat base with a dry side recess and a wet side recess next to the dry side recess;
  a drying pad received in the dry side recess; and
  a wet station received in the wet side recess, the wet station including (i) a pan for holding a pool of disinfecting solution, (ii) an elastomeric cover covering the pan and the pool of disinfecting solution therein, the elastomeric cover having a plurality of openings and a plurality of raised nubbins distributed thereon, and (iii) a fluid reservoir, the fluid reservoir being in fluid communication with the pan by way of an on/off valve, the reservoir being at least partially filled with disinfecting solution;
  wherein the plurality of openings are (i) integral to the elastomeric cover, (ii) defined between a thickness of the elastomeric cover and distributed thereon, and (iii) normally closed and open to allow solution therethrough when the elastomeric cover is stepped upon and stretched.

18. The floor mat assembly of claim 17, wherein the elastomeric cover is tautly received over the pan.

19. The floor mat assembly of claim 18, wherein the pan has a bottom surface and includes one or more upwardly-extending raised ridges disposed thereon.

20. A method of using the floor mat assembly of claim 1 comprising:
  stepping on the elastomeric cover with both feet while wearing shoes causing the cover to sink into the pan and disinfecting solution to rise through the plurality of holes to wet soles of the shoes;
  moving the soles over the surface of the cover to ensure the soles are fully wetted;
  without stepping on any other surface moving the feet over to the drying pad; and
  moving the soles against the dry pad to dry them.

* * * * *